United States Patent
Rapsomaniki et al.

(10) Patent No.: US 11,475,275 B2
(45) Date of Patent: Oct. 18, 2022

(54) RECURRENT AUTOENCODER FOR CHROMATIN 3D STRUCTURE PREDICTION

(71) Applicant: International Business Machines Corporation, Armonk, NY (US)

(72) Inventors: Maria Anna Rapsomaniki, Zurich (CH); Bianca-Cristina Cristescu, Zurich (CH); Maria Rodriguez Martinez, Thalwil (CH)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 641 days.

(21) Appl. No.: 16/515,159

(22) Filed: Jul. 18, 2019

(65) Prior Publication Data
US 2021/0019598 A1    Jan. 21, 2021

(51) Int. Cl.
*G06E 1/00* (2006.01)
*G06E 3/00* (2006.01)
(Continued)

(52) U.S. Cl.
CPC ......... *G06N 3/0445* (2013.01); *G06N 3/0454* (2013.01); *G06N 3/084* (2013.01); *G06N 3/088* (2013.01); *G16B 15/10* (2019.02)

(58) Field of Classification Search
CPC .... G06N 3/0445; G06N 3/0454; G06N 3/084; G06N 3/088; G16B 15/10; G16B 40/20
See application file for complete search history.

(56) References Cited

U.S. PATENT DOCUMENTS

2017/0329892 A1* 11/2017 Fan .................. G16B 50/30
2018/0245079 A1   8/2018 Lieberman et al.
(Continued)

FOREIGN PATENT DOCUMENTS

WO      2018006152 A1    1/2018

OTHER PUBLICATIONS

Santana, Eder, Matthew Emigh, and Jose C. Principe. "Information theoretic-learning auto-encoder." 2016 International Joint Conference on Neural Networks (Ijcnn). IEEE, 2016. (Year: 2016).*
(Continued)

*Primary Examiner* — Luis A Sitiriche
*Assistant Examiner* — Sidney Vincent Bostwick
(74) *Attorney, Agent, or Firm* — Cantor Colburn LLP; Daniel Morris

(57) ABSTRACT

A computer-implemented method for inferring a 3D structure of a genome is provided. The method includes providing genome interaction data and operating an autoencoder including a structured sequence of n autoencoder units, each of which including an encoder unit and a decoder unit, each of which is implemented as a recurrent neural network unit. The method includes additionally training the autoencoder by feeding all vectors of genome interaction data to the encoder units. Thereby, the training of the auto-encoder units is performed stepwise by using inner state of respective previous autoencoder units in the cascaded sequence of autoencoder units and performing backpropagation within each of the plurality of autoencoder units after all autoencoder units have processed their respective input values, and using the output values of the encoder units for deriving a 3D model for a visualization of the genome.

23 Claims, 7 Drawing Sheets

(51) Int. Cl.
G06F 15/18 (2006.01)
G06G 7/00 (2006.01)
G06N 3/04 (2006.01)
G06N 3/08 (2006.01)
G16B 15/10 (2019.01)

(56) References Cited

U.S. PATENT DOCUMENTS

2020/0226797 A1* 7/2020 Schroers ............... G06T 9/20
2021/0163930 A1* 6/2021 Clarke ................. C12N 15/113

OTHER PUBLICATIONS

Qiao, Yi-Ling, et al. "Learning bidirectional LSTM networks for synthesizing 3D mesh animation sequences." arXiv preprint arXiv:1810.02042 (2018). (Year: 2018).*
Park, Seong Hyeon, et al. "Sequence-to-sequence prediction of vehicle trajectory via LSTM encoder-decoder architecture." 2018 IEEE Intelligent Vehicles Symposium (Iv). IEEE, 2018. (Year: 2018).*
Xiong, Kyle, and Jian Ma. "Revealing Hi-C subcompartments by imputing high-resolution inter-chromosomal chromatin interactions. " bioRxiv (2018): 505503. (Year: 2018).*
Yan, Koon-Kiu, et al. "HiC-spector: a matrix library for spectral and reproducibility analysis of Hi-C contact maps." Bioinformatics 33.14 (2017): 2199-2201. (Year: 2017).*
Tolstikhin, Ilya, et al. "Wasserstein auto-encoders." arXiv preprint arXiv:1711.01558 (2017). (Year: 2017).*
Farré, Pau, et al. "Dense neural networks for predicting chromatin conformation." BMC bioinformatics 19.1 (2018): 1-12. (Year: 2018).*
Baù et al., "The three-dimensional folding of the α-globin gene domain reveals formation of chromatin globules," Nature Structural & Molecular Biology 18.1 (2011): 107-114.
Bonev et al., "Organization and function of the 3D genome," Nature Reviews Genetics 17.11 (2016): 661-678.
Dekker et al., "Capturing Chromosome Conformation," Science 295.5558 (2002): 1306-1311.
Dekker et al., "The 4D nucleome project," Nature 549.7671 (2017): 219-226.
Dekker, "Gene regulation in the third dimension," Science 319.5871 (2008): 1793-1794.
Deng et al., "A sparse autoencoder-based deep neural network for protein solvent accessibility and contact number prediction," BMC bioinformatics 18.16, 2017, 10 pages.
Duan et al., "A Three-Dimensional Model of the Yeast Genome," Nature 465.7296 (2010): 363-367.
Duggal et al., "Higher-order chromatin domains link eQTLs with the expression of far-away genes," Nucleic Acids Research 42.1 (2013): 87-96.
Farré et al., "Dense neural networks for predicting chromatin conformation," BMC bioinformatics 19.1, 2018, 12 pages.
Fraser et al., "Nuclear organization of the genome and the potential for gene regulation," Nature 447.7143 (2007): 413-417.
Gaietta et al., "Multicolor and Electron Microscopic Imaging of Connexin Trafficking," Science 296.5567 (2002): 503-507.
Gonzalez-Sandoval et al., "Perinuclear Anchoring of H3K9-Methylated Chromatin Stabilizes Induced Cell Fate in C. elegans Embryos," Cell 163.6 (2015): 1333-1347.
Hochreiter et al., "Long short-term memory," Neural computation 9.8 (1997): 1735-1780.
Hu et al., "Bayesian Inference of Spatial Organizations of Chromosomes," PLoS Computational Biology 9.1 (2013): e1002893.

Kruskal, "Multidimensional scaling by optimizing goodness of fit to a nonmetric hypothesis," Psychometrika 29.1 (1964): 1-27.
Lesne et al., "3D genome reconstruction from chromosomal contacts," Nature Methods 11.11 (2014): 1141.
Lieberman-Aiden et al., "Comprehensive mapping of long-range interactions reveals folding principles of the human genome," Science 326.5950 (2009): 289-293.
Miele et al., "Long-range chromosomal interactions and gene regulation," Molecular Biosystems 4.11 (2008): 1046-1057.
Misteli, "Beyond the Sequence: Cellular Organization of Genome Function," Cell 128.4 (2007): 787-800.
Misteli, "Spatial Positioning: A New Dimension in Genome Function," Cell 119.2 (2004): 153-156.
Mitelman et al.,"The impact of translocations and gene fusions on cancer causation," Nature Reviews Cancer 7.4 (2007): 233-245.
Oluwadare et al., "A maximum likelihood algorithm for reconstructing 3D structures of human chromosomes from chromosomal contact data," BMC Genomics 19.1 (2018): 161.
Park et al., "Impact of data resolution on three-dimensional structure inference methods," BMC Bioinformatics 17.1 (2016): 70.
Rieber et al., "miniMDS: 3D structural inference from high-resolution Hi-C data," Bioinformatics 33.14 (2017): i261-i266.
Rousseau et al., "Three-dimensional modeling of chromatin structure from interaction frequency data using Markov chain Monte Carlo sampling," BMC Bioinformatics 12.1 (2011): 414.
Rust et al., "Sub-diffraction-limit imaging by stochastic optical reconstruction microscopy (STORM)," Nature Methods 3.10 (2006): 793-796.
Tanizawa et al., "Mapping of long-range associations throughout the fission yeast genome reveals global genome organization linked to transcriptional regulation," Nucleic Acids Research 38.22 (2010): 8164-8177.
Therizols et al., "Chromatin decondensation is sufficient to alter nuclear organization in embryonic stem cells," Science 346.6214 (2014): 1238-1242.
Trieu et al., "Large-scale reconstruction of 3D structures of human chromosomes from chromosomal contact data," Nucleic Acids Research 42.7 (2014): e52.
Trussart et al., "Assessing the limits of restraint-based 3D modeling of genomes and genomic domains," Nucleic Acids Research 43.7 (2015): 3465-3477.
Van der Maaten et al., "Visualizing Data Using t-SNE," Journal of Machine Learning Research 9 (2008): 2579-2605.
Van Steensel et al., "Genomics tools for unraveling chromosome architecture," Nature Biotechnology 28.10 (2010): 1089-1095.
Varoquaux et al., "A statistical approach for inferring the 3D structure of the genome," Bioinformatics 30.12 (2014): i26-i33.
Wachter et al., "On the implementation of an interior-point filter line-search algorithm for large-scale nonlinear programming," Mathematical Programming 106.1 (2006): 25-57.
Nang et al., "Inferential modeling of 3D chromatin structure," Nucleic Acids Research 43.8 (2015): e54.
Nang, "Classical Multidimensional Scaling," in Geometric Structure of High-Dimensional Data and Dimensionality Reduction. Heidelberg: Springer, 2012, pp. 115-129.
Zhang et al., "3D Chromosome Modeling with Semi-Definite Programming and Hi-C Data," Journal of Computational Biology 20.11 (2013): 831-846.
7Hu et al., "Reconstructing spatial organizations of chromosomes through manifold learning," Nucleic Acids Research 16.8 (2018): e50.
Zou et al., "HSA: integrating multi-track Hi-C data for genome-scale reconstruction of 3D chromatin structure," Genome Biology 17.1 (2016): 40.

* cited by examiner

Require: X: HiC contact frequency matrix
T: number of time points
N: sequence length and the features dimensionality
D: dimensionality of the embedding
E: number of epochs
Ensure: $X \in \mathbb{R}^{T \times N \times N}$
1: Initialize first time point weights randomly $W^{enc}_0, W^{dec}_0$
2: for $t = 1, 2, \ldots, T$ do
3:    Initialize the network weights $W^{enc}_t = W^{enc}_{t-1}$
     $W^{dec}_t = W^{dec}_{t-1} \in \mathbb{R}^{N \times d}$
4:    $Z \in \mathbb{R}^{T \times N \times d}$ embeddings; 0-state embed. $z_0 = (0, 0, 0)$
5:    for epoch = $1, 2, \ldots, E$ do
6:      for $i = 1, 2, \ldots, N$ do
7:        Encode the input $x^t_i, i \in \mathbb{R}^N$ into $z^t_i \in \mathbb{R}^d$
8:        Decode $z^t_i \in \mathbb{R}^d$ into the recon. $\hat{x}^t_i, i \in \mathbb{R}^N$
9:      end for
10:     update $W^{end}_t, W^{end}_{t-1} \nabla L$, i.e. the gradient of the loss in Equation 3
11:    end for
12: end for
13: return $Z \in \mathbb{R}^{T \times N \times d}$

FIG. 4

RECURRENT AUTOENCODER FOR CHROMATIN 3D STRUCTURE PREDICTION

BACKGROUND

The invention relates generally to an inference method for genomes, and more specifically, to a computer-implemented method for inferring a 3D structure of a genome. The invention relates further to a related inference system for inferring a 3D structure of a genome, and a computer program product.

Genome research has made important progress in the last year on the way to a more complete understanding of the complete complexity of genomes. In eukaryotic cells, the total length of the DNA molecule exceeds by far the diameter of the nucleus. To fit in the nucleus it is carefully packaged around specific proteins, forming a complex called chromatin. Despite this high degree of compaction, DNA, in its uncompressed form, must be rapidly accessible to a variety of protein machineries that regulate the essential functions of life, such as DNA replication, transcription and translation.

Recent studies have revealed that chromatin folding his non-randomly organized within a cell's nucleus. There are different hierarchical levels and compact regions, called topology associated domains (TADs). If two genomic fragments are close in the linear DNA sequence, they are also close in the three-dimensional (3D) structure, but the converse is not necessarily true. Multiple studies have associated chromatin folding with gene-gene interactions and gene regulation because genomically distant regions that participate in functional interactions have been shown to be located in closer proximity in 3D space than expected at chance. Similar observations have been made in a variety of vital cellular functions.

Understanding the 3D format and confirmation is essential for decoding and interpreting the functions of the genome as a whole, as well as its functional and regulatory elements, and can provide a mechanistic explanation of various biological processes and their links to human diseases. Despite the advancements in using microscopy techniques, it became clear that they are limited to a small number of genomic bins and do not support a comprehensive analysis of the complete genome structure.

In recent years, the advancements in chromosome confirmation capture (3C) techniques have paved the way for a systematic analysis of the 3D structure of chromatin. 3D-based methods provide measurements of the physical interaction frequency between genomic regions in the chromatin. E.g., HiC is a high-throughput, high-resolution 3C-based method which quantifies intra- and inter-chromosomal interaction frequencies at all-genome scale. Chromatin interactions captured by HiC are represented as a contact matrix where each entry determines the frequency of interactions between a pair of genomic regions (bins) at a given resolution for a population of cells. Therefore, one of the applications of HiC data is to reconstruct the 3D structure of the genome from the contact matrix.

Most methods developed, and thus found the literature for this task, can be classified into optimization-based and modeling-based methods. Because naturally distance and frequency are inversely correlated, optimization methods model this relationship with a specific function, called transfer function, used to transform the contact matrix into a distance matrix. However, this approach has also its limitations that reduces the usability of the known methods. Finally, none of the existing methods can perform a dynamic analysis of chromatin structures because they do not account for incorporating time-course information in the 3D chromatin structure prediction.

Embodiments of the invention described herein provide a computer-implemented method to reconstruct the 3D structure of the genome from the contact matrix.

SUMMARY

According to aspects of the present invention, a computer-implemented method for inferring a 3D structure of a genome is provided. A non-limiting example of the computer-implemented method can include providing an n*n matrix of genome interaction data, and operating an autoencoder including a structured sequence of n autoencoder units, each of which including an encoder unit and a decoder unit. Thereby, each of the encoder units and each of the decoder units can be implemented each as a recurrent neural network unit.

The computer-implemented method can further include training the autoencoder by feeding all n vectors of the matrix of genome interaction data to input layers of the n encoder units until the fed n vectors of genome interaction data and respective decoder outputs only differ by a predefined threshold value. Thereby, the training of the autoencoder units can be performed stepwise by using as input for an ith selected encoder unit the respective ith vector of the genome interaction data, and output values of the previous encoder unit to the selected encoder unit in the structured sequence of n autoencoder units. The stepwise training can include as well using as input for an ith selected decoder unit output values of the ith encoder unit, and output values of the previous decoder unit to the selected decoder unit in the structured sequence of n autoencoder units.

Furthermore, the computer-implemented method can include performing backpropagation within each of the plurality of autoencoder units after all autoencoder units have processed their respective input values.

The computer-implemented method can include using the output values of the encoder units for deriving a 3D model for a visualization of the genome.

According to another aspect of the present invention, an inference system for inferring a 3D structure of a genome is provided. The inference system can include a receiving unit adapted for providing an n*n matrix of genome interaction data, and an autoencoder system including a structured sequence of n autoencoder units, each of which including an encoder unit and a decoder unit, wherein each of the encoder units and each of the decoder units is implemented each as a recurrent neural network unit.

The inference system can further include a training module adapted for training the autoencoder by feeding all n vectors of the matrix of genome interaction data to input layers of the n encoder units until the fed n vectors of genome interaction data and respective decoder outputs only differ by a predefined threshold value. Thereby, the training of the autoencoder units can be performed stepwise by using as input for an ith selected encoder unit the respective ith vector of the genome interaction data, and output values of the previous encoder unit to the selected encoder unit in the structured sequence of n autoencoder units. Additionally, the inference system can include performing backpropagation within each of the plurality of autoencoder units after all autoencoder units have processed their respective input values.

Last but not least, the inference system include a visualization module adapted for using the output values of the encoder units for deriving a 3D model for a visualization of the genome.

The proposed computer-implemented method for inferring a 3D structure of a genome—as well as the related device—can offer multiple advantages and technical effects:

The proposed concept can allow an elegant way to reconstruct and visualize a 3D chromatin structure at the bin-level from a contact matrix. The usage of a transfer function from a determined contact frequency to distances—either probabilistic or non-probabilistic—is not required. The reconstruction can be achieved by inferring structures at a high resolution of about 20 Kb down to 5 Kb (kilo-bases) and reasonable computational time; thereby the high-dimensionality of HiC data is taken into account.

This can also allow a time-dependent analysis so that dynamic behaviors and structures of the genome can be analyzed and studied. Also for this, only reasonable computational time may be required to perform the analysis on the whole genome and changes in chromatin conformation over time. Additionally, the sequence of the bins in the genome can be preserved.

The proposed computer-implemented method and the related system can also work on the basis of sparse contact matrices. Thereby, the local as well as the global structure of the chromatin can be reflected.

It is noted that data from a population of cells can be usable so that an ensemble of structures can be inferred and predicted.

Hence, the computer-implemented method can have a significant influence on the process of elucidating genome regulation and the aberrations that potentially lead to human diseases. Hidden information in the 3D structure of chromatin can be researched. Furthermore, the 3D structures inferred by the proposed concept can also be exploited in simulation studies, such as a DNA replication model.

In the following, additional embodiments of the inventive concept—applicable for the computer-implemented method as well as for the system—will be described.

According to one possible embodiment of the computer-implemented method, the genome interaction data originate from a publicly available source. Thus, there is no lack of training data, e.g., HiC matrices. Of course, beside publicly available sources for genome interaction data, also nonpublic data can be used.

According to embodiments of the computer-implemented method, the matrix of the genome interaction data originate from an HiC experiment. Such data also often referred to as contact matrix and can be derived from High-resolution Chromosome Conformation Capture.

According to one advantageous embodiment of the computer-implemented method, the output values of the encoder units are used as coordinates in 3-dimensional space. This can allow elegantly visualizing bins of genomes in 3D space, wherein each of the 3D coordinate can relate to a location of a specific bin.

According to an additionally advantageous embodiment of the computer-implemented method, each of the recurrent neural network units is an LSTM—i.e., in particular a Long Short-Term Memory—neural network unit. An LSTM can refer a special implementation architecture of a recurrent neural network. LSTMs have the required feedback connections allowing not only to processing the data points but also entire sequences of data. LSTMs have also an advantage in handling time-series data because that can be lax of unknown durations between events in a timeseries. However, also other types of RNNs can be used, like, e.g., GRU (Gated Recurrent Units). Also these types or RNNs can be implemented having the ability to forget what it seen in longer sequences, thus having a short-term memory. Hence, these RNNs can be trained to keep only relevant information to make predictions, and forget non relevant data.

According to embodiments of the computer-implemented method, each vector of the n*n matrix of genome interaction data can represent contact information of a bin of the genome. Thus, each vector of the matrix—e.g., either horizontal or vertical—can be handled technically independently of the other bin's contact data by feeding the vectors to separate autoencoder units, i.e., related input layers of the related decoder units.

According to one optional embodiment of the computer-implemented method, a loss function—in particular, for the optimization process during the training—of each of the encoder units and decoder units can be cell-type—i.e., biological cell—specific. However, other implementations can allow using a cell-type independent loss function. Thus, this can allow a wide variety of different implementation options.

According to embodiments of the computer-implemented method, a loss function can include a reconstruction cost factor and a distance cost factor. More details are disclosed in the context with equation (3) in this document (see below).

According to embodiments of the computer-implemented method, the reconstruction cost factor can be determined according to a mean-square error loss calculation. More details are disclosed in the context of equation (4) in this document (see below).

According to embodiments of the computer-implemented method, the distance cost factor can act as a regularizer on the lower-bound and upper-bound of the Euclidean distance between two consecutive bins of a genome. More details are disclosed in the context of equation (5) in this document (see below).

According to embodiments of the invention, the computer-implemented method can also include providing a timeseries of genome interaction data—i.e., a timeseries of contact matrices—to the autoencoder, and using resulting time-dependent output values of the encoder units for deriving a time-dependent 3D model for a visualization of the genome. Using this approach, a moving/vibrating genome can be visualizable in order to study interactions of specific portions of a genome with other portions of the same genome or with other genomes. This can enhance the understanding of complex genome structures and their behavior in the time dimension.

According to embodiments of the computer-implemented method, the providing the time series of genome interaction data to the autoencoder can also include initializing, during the training phase, weight factors of the encoder units and decoder units with respective weight factors of a previous time point of the time series of genome interaction data, in particular from the predecessor autoencoder units in the structured sequence of autoencoder units. This can have the effect that the training time for the overall autoencoder including the plurality of autoencoder units can be reduced. This can also be supported by the fact that the positions of the structure at the previous time point was taken into account.

Furthermore, embodiments of the invention can take the form of a related computer program product, accessible from a computer-usable or computer-readable medium providing program code for use, by, or in connection, with a computer or any instruction execution system. For the purpose of this description, a computer-usable or computer-readable medium can be any apparatus that contains means for storing, communicating, propagating or transporting the program for use, by, or in connection, with the instruction execution system, apparatus, or device.

BRIEF DESCRIPTION OF THE DRAWINGS

It should be noted that embodiments of the invention are described with reference to different subject-matters. In particular, some embodiments are described with reference to method type claims, whereas other embodiments are described with reference to apparatus type claims. However, a person skilled in the art will gather from the above and the following description that, unless otherwise notified, in addition to any combination of features belonging to one type of subject-matter, also any combination between features relating to different subject-matters, in particular, between features of the method type claims, and features of the apparatus type claims, is considered as to be disclosed within this document.

The aspects defined above, and further aspects of the present invention, are apparent from the examples of embodiments to be described hereinafter and are explained with reference to the examples of embodiments, but to which the invention is not limited.

Figure 1:
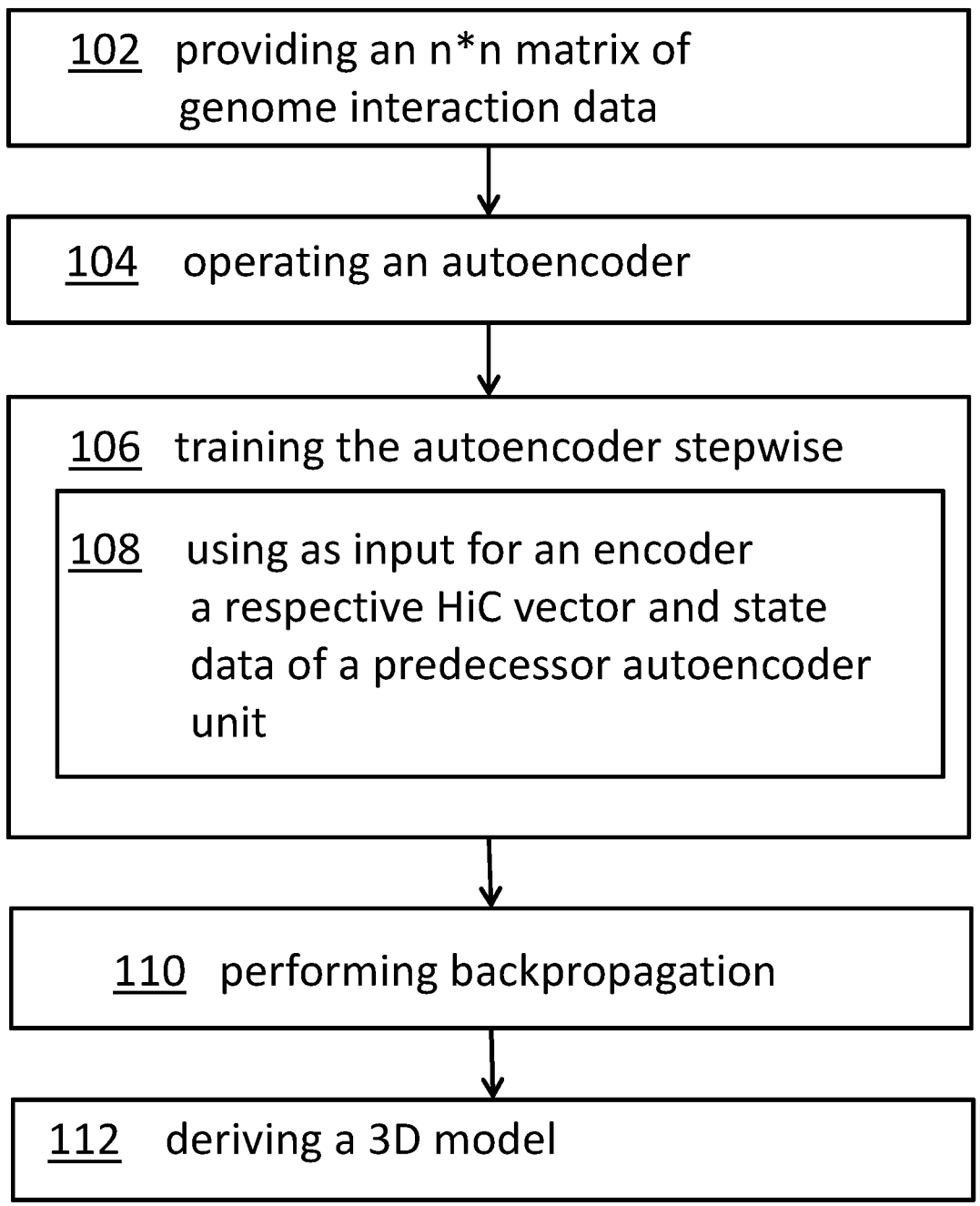

Embodiments of the invention will be described, by way of example only, and with reference to the following drawings:

FIG. 1 shows a block diagram of an embodiment of the inventive computer-implemented method for inferring a 3D structure of a genome.

Figure 2:
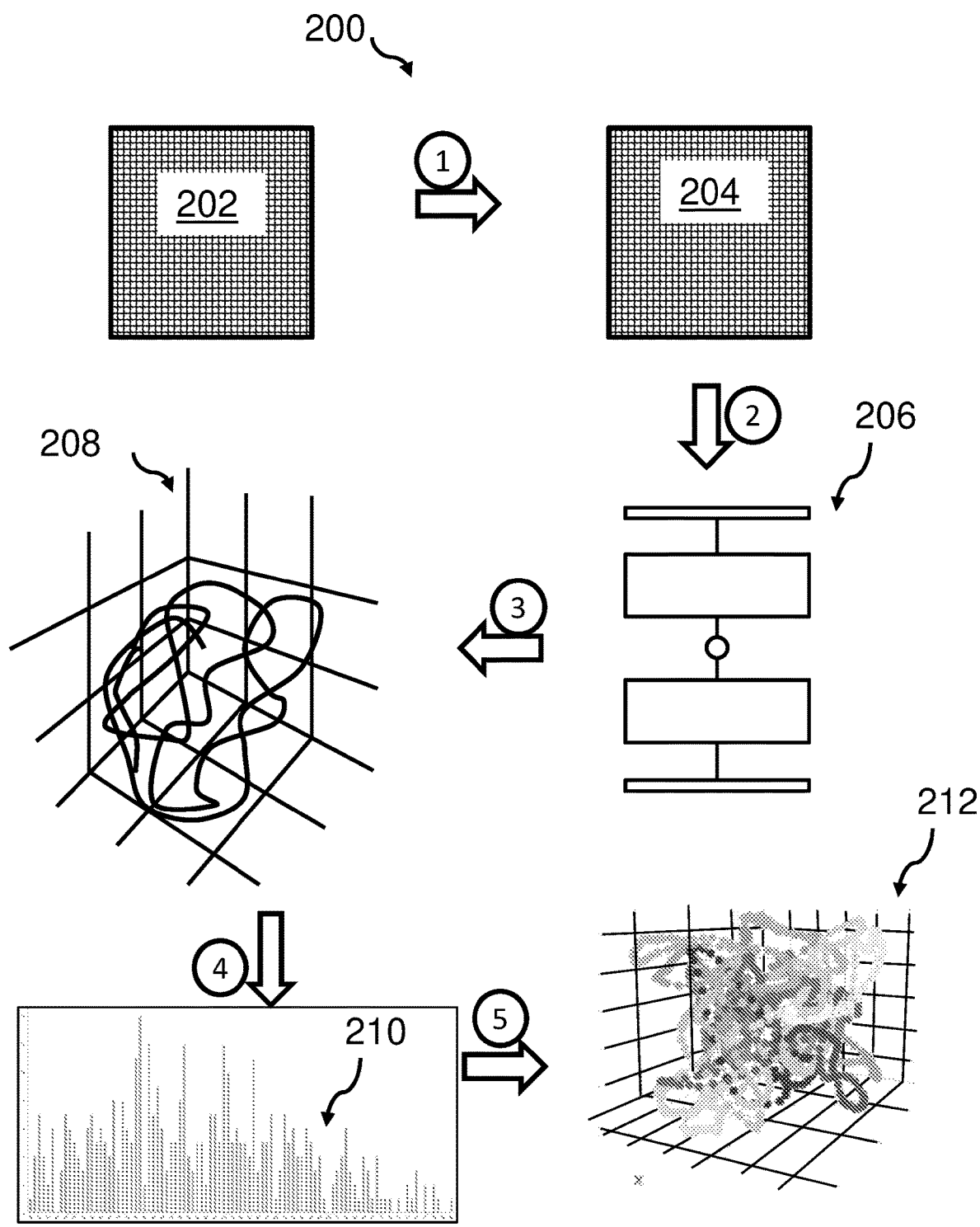

FIG. 2 shows a block diagram of a workflow 200 for predicting and visualizing the chromatin folding.

Figure 3:
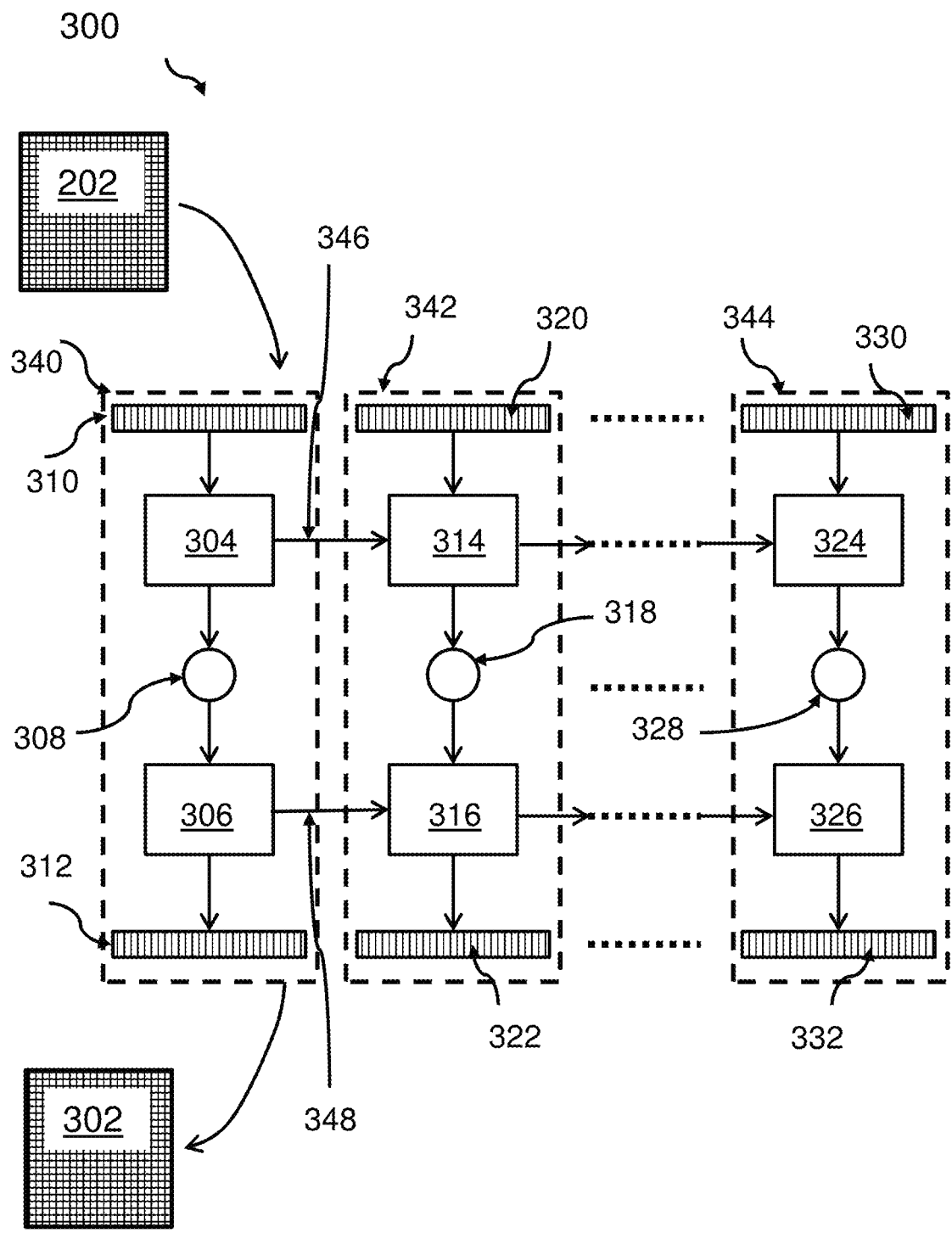

FIG. 3 shows a block diagram of an embodiment of the autoencoder including a cascaded sequence of autoencoder units.

FIG. 4 shows an embodiment of pseudocode for the here proposed computer-implemented method for the case of contact data being available as timeseries data.

Figure 5:
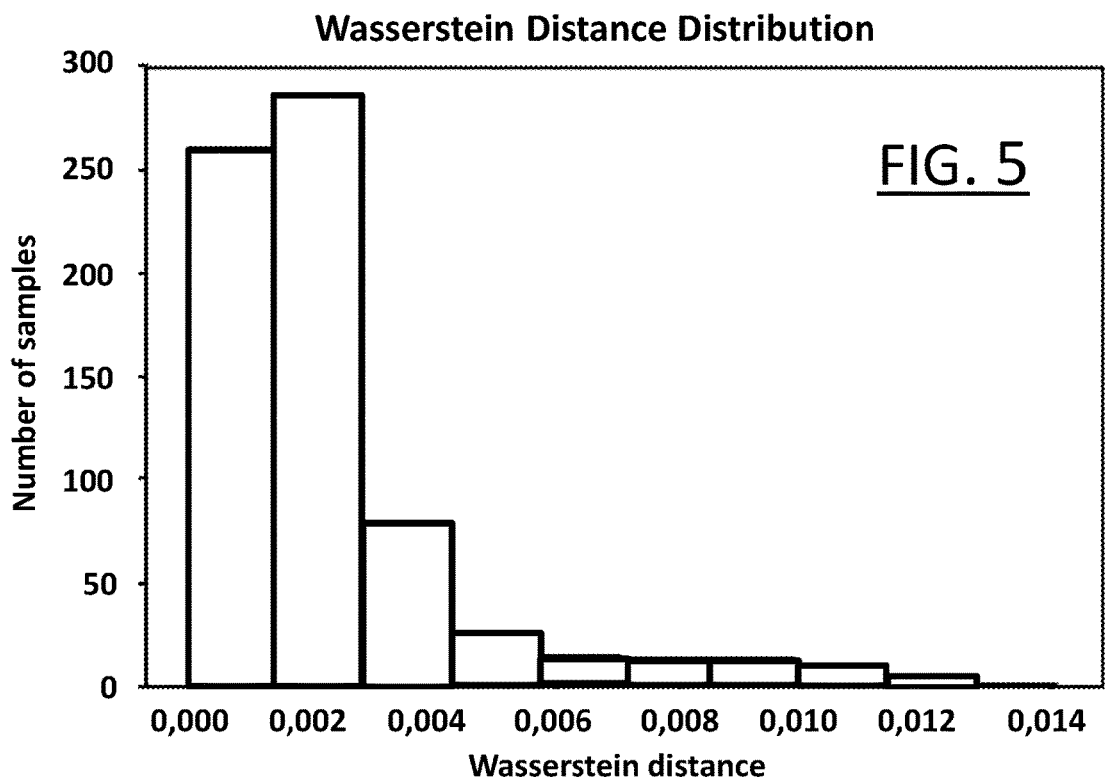

FIG. 5 shows a diagram of experimental results using Wasserstein distances across all pairs of bins.

Figure 6:
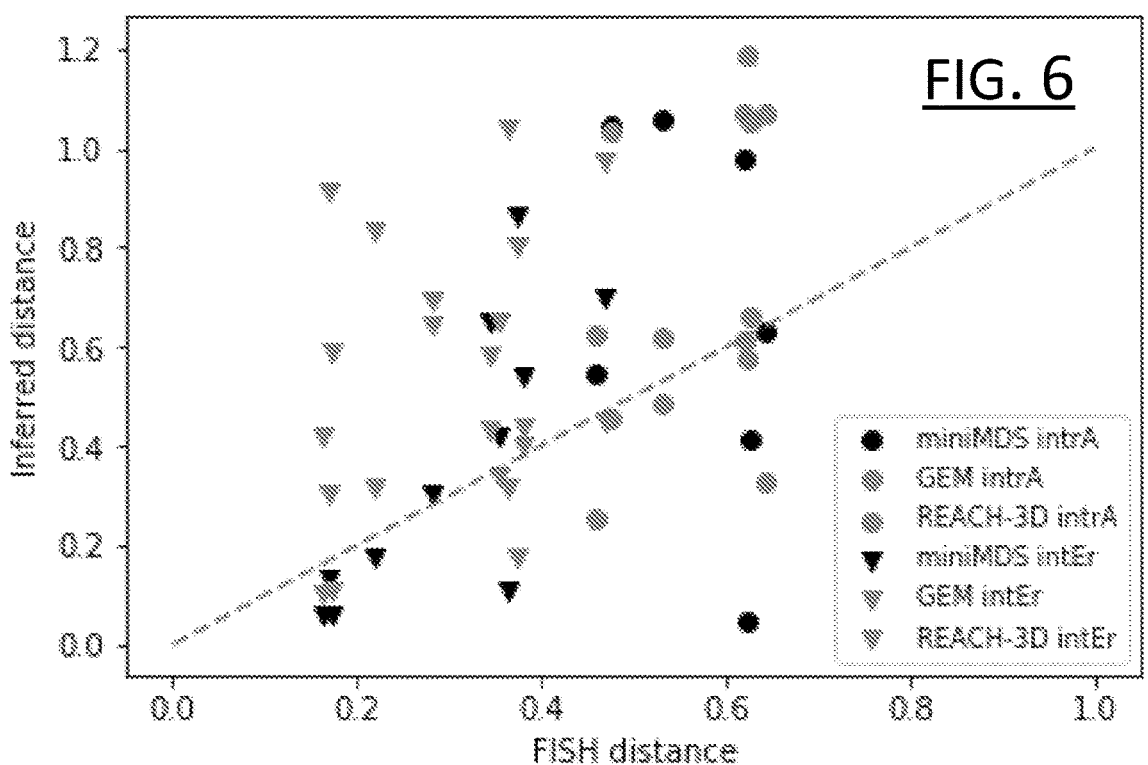

FIG. 6 shows a diagram of experimental results of a correlation of distances measured by fish imaging and distances obtained in the inferred structures between 18 pairs of bins (11 intra and 7 inter-chromosomal).

Figure 7:
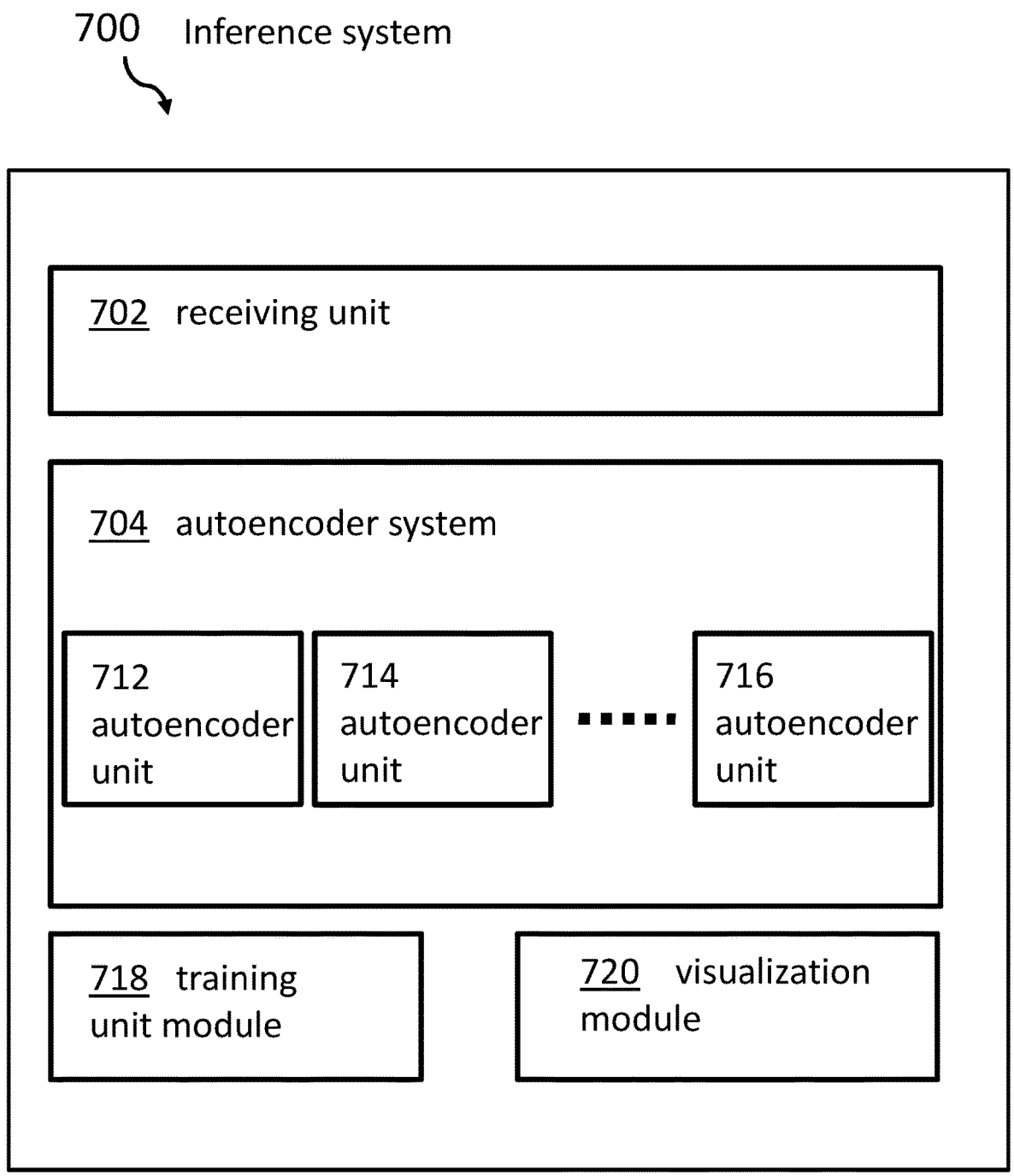

FIG. 7 shows a block diagram of an embodiment of the proposed inference system.

Figure 8:
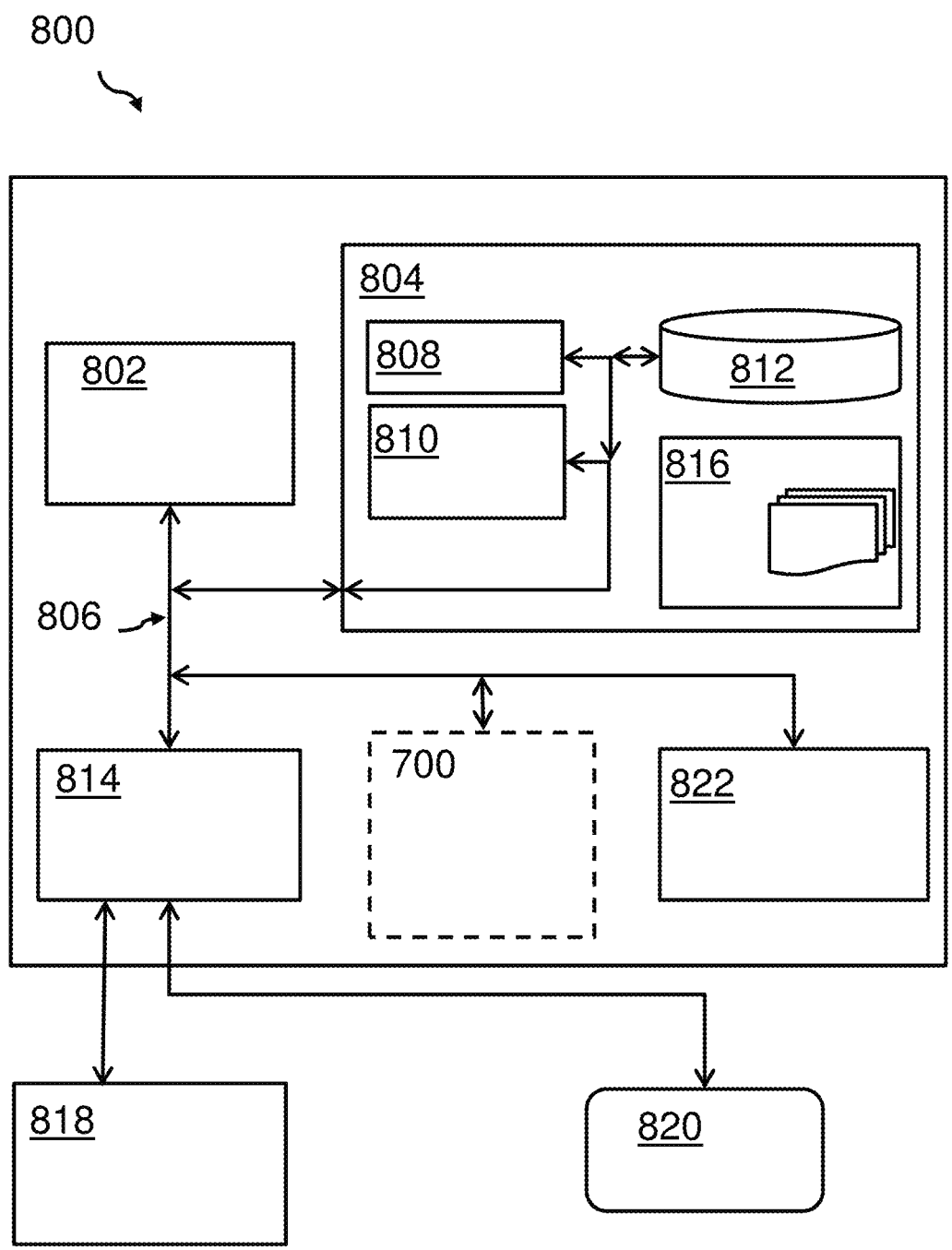

FIG. 8 shows a block diagram of an embodiment of a computing system including the inherent system according to FIG. 7.

DETAILED DESCRIPTION

In the context of this description, the following conventions, terms and/or expressions may be used:

The term "inferring" may denote the process of using an inference engine—which may be part of a larger inference system—that may apply logical rules to a knowledge base to deduce new information. In the proposed concept, the inference system may be trained with experimentally derived contact information of genomes to predict a 3D appearance of a genome.

The term "3D structure" may denote a physical entity being describable by coordinates in the 3-dimensional space. A projection of the 3-dimensional space to the 2-dimensional space may allow to print the 3D structure on paper or visualize the 3D structure on a computer screen The term "genome" may denote the genetic material of an organism. It may consist of a DNA. DNAs may be linked to specific protein structures building chromatin.

The term "genome interaction data" may denote experimentally derived HiC data or an HiC matrix. Such data are also often referred to as contact matrix and may be derived from High-resolution Chromosome Conformation Capture.

The term "autoencoder" may denote a special type of an artificial neural network to learn data encodings in an unsupervised manner. The aim of an autoencoder is to learn a representation (i.e., an encoding) a set of data, typically for dimensionality reduction—e.g., down to 3D coordinates—by training the network to ignore signal noise. Along with the reduction side, a reconstruction side is trained, wherein the autoencoder may try to generate from the reduced encoding a representation as close as possible to the original input. The unsupervised manner may be achieved by comparing the input data and output data and determine a difference between those in order to determine a stop criteria for the training.

The term "autoencoder unit" may here refer to a sub-unit of a "larger autoencoder". Hence, the larger autoencoder may include a plurality of autoencoder units or autoencoder cells which may be cascaded—i.e., linked to each other in a specific architecture—in order to receive vectors of a matrix—in particular the contact matrix—as a whole.

The term "encoder unit" may denote the reductions side of an autoencoder, i.e., a layered structure of artificial neurons wherein the number of artificial neurons is reduced from layer to layer from the input side to the output side.

The term "decoder unit" may denote the reconstruction portion of an autoencoder. It may take the output of a related encoder in order to reconstruct the original input data.

The term "recurrent neural network" (RNN) may denote a specific class of artificial neural networks in which connections between nodes may form a directed graph along a temporal sequence. This may allow it to exhibit a temporal dynamic behavior. Unlike feedforward neural networks, RNNs can use their internal state (memory) to process sequences of inputs. This may position RNNs advantageous for contact matrix data.

The term "input layer" may denote a first layer of a neural network. The number of artificial neurons may be identical—or similar to—the dimension of an input vector to the neural network. In the proposed concept, the size of the input layer—i.e., the number of artificial neurons—may be equal to the dimension of the contact matrix.

The term "stepwise"—in particular a stepwise training of the autoencoder—may denote here that the autoencoder units may be trained in a cascaded approach. This may particularly the be useful because a subsequent autoencoder unit may use output data (e.g., the internal state) of the predecessor autoencoder unit.

The term "backpropagation" may denote the method to determine a gradient needed in the determination of weights of artificial neurons in neural networks, like RNNs. The term back-propagation may also be seen as a shortcut for "a backwards propagation of errors", because an error is determined at the output of the neural network and distributed backwards through the network layers. It may also be noted that back propagation is a special case of a more general technique denoted as automatic differentiation. In the context of learning or training, backpropagation is commonly used by gradient descent optimization algorithms to adjust individual weight values of artificial neurons by determining the gradient of a loss function.

The term "3D model for a visualization of the genome" may denote geometrical representation of a genome in the 3-dimensional space which may be visualized using computer screens.

The term "HiC experiment" may denote High-Resolution Chromosome Conformation Capture techniques.

The term "LSTM neural network unit" may denote a "Long Shot-Term Memory" used as one implementation method of an RNN. The special feedback connections of an LSTM make it—unlike feedforward neural networks—a more or less "general purpose computer", i.e., it may be enabled to compute anything that a Turing machine also can.

The term "bin" may denote a portion of a genome; here, a typical bin size would be in the range of 20 kilobases to 5 kilobases or also 50 kilobases down to 1 kilobases. With advancing technologies and analysis precision even better resolutions may be possible. However, the proposed concept is not limited to any specific bin resolution.

The term "loss function" may denote a term often used in computational neuroscience and machine learning and may also be noted as cost function that maps an event of values of one or more variables onto a real number intuitively representing some of the "costs" associated with the event. An optimization problem may seek to minimize a loss function.

The term "reconstruction cost factor" may relate to the loss function relating to both, the encoder and decoder portion and their working together.

The term "distance cost factor" may relate to a loss function related to a distance of bins of the genome or vectors of the contact matrix. An example may be the Wasserstein distance, the Euclidean distance or the experimental determined FISH (Fluorescent In Situ Hybridization) distance.

The term "timeseries of genome interaction data" may denote a plurality of HiC matrices of the same genome at different points in time.

In the following, a detailed description of the figures will be given. All instructions in the figures are schematic. Firstly, a block diagram of an embodiment of the inventive computer-implemented method for inferring a 3D structure of a genome is given. Afterwards, further embodiments, as well as embodiments of the inference system for inferring a 3D structure of a genome, will be described.

FIG. 1 shows a block diagram of an embodiment of the computer-implemented method 100 for inferring a 3D structure of a genome, the method includes providing, 102, an n*n matrix of genome interaction data, in particular an HiC matrix, and operating, 104, an autoencoder including a structured sequence of n autoencoder units for each vector of the HiC matrix. Each of the autoencoders includes an encoder unit and a decoder unit, wherein each of the encoder units and each of the decoder units are implemented each as a recurrent neural network unit.

The method 100 also includes training, 106, the autoencoder by feeding all n vectors of the matrix of genome interaction data to input layers of the n encoder units until the fed n vectors of genome interaction data and respective decoder outputs only differ by a predefined threshold value.

The training of the auto-encoder units is performed stepwise by using, 108, as input for an ith selected ith encoder unit—e.g., with the exception of the 1st one—the respective ith vector of of genome interaction data, and output values of the previous encoder unit, i.e., the inner state of encoder i−1—the selected encoder unit i in the structured sequence of n autoencoder units. Furthermore, as input values for an ith selected decoder unit output values of the ith encoder unit, and output values of the previous decoder unit (i.e., i−1) to the selected decoder unit in the structured sequence of n autoencoder units are used. Thus, the inner state of a previous autoencoder unit—for the encoder as well as for the decoder—is used for a selected autoencoder unit. The respected inner states of an autoencoder unit are represented by the output value of respective encoders/decoders.

The method 100 includes as well performing, 110, backpropagation within each of the plurality of autoencoder units after all autoencoder units have processed their respective input values, and using the output values of the encoder units—particularly, as many as there are vectors in the contact matrix, i.e., number of bins in the matrix—for deriving, 112, a 3D model for a visualization of the genome and visualize the results in a 2D projection of the 3D model, i.e., positions of the bins of the genome, either static or in a time-dependent fashion.

FIG. 2 shows a block diagram of a workflow 200 for predicting and visualizing the chromatin folding. The input to the used framework is the HiC contact matrix 202. The matrix 202 is then pre-processed for obtaining the right data format and form of the matrix 204. This transition is indicated by arrow "1" in FIG. 2. The next step indicated by the transformation arrow "2" is running the matrix data through a network 202 of autoencoders (206). This generates as output—indicated by transformation arrow "3"—3D coordinates 208 of chromatin bins for one or a plurality of time points. Then, a post-processing step—indicated by transformation arrow "4"—may align the 3D ensemble of structures to prepare them for a validation and evaluation step (210). Finally, the inferred structure can be visualized, as shown in the diagram 212.

Before describing the next figure, a couple of considerations and assumptions for the here proposed method "REcurrent Autoencoders for CHromatin 3D structure prediction"—in short REACH-3D—may be made.

To apply manifold learning to the problem at hand, it is assumed that the 3D structure of the chromatin lies in the 3D manifold. Thus, the bins are presented as points in 3D space. This manifold is, so to speak, embedded in the high-dimensional space of the interaction frequencies through the HiC experiment entry presented by the contact matrix $C \in \mathbb{R} D$. What manifold learning tries to achieve is to reduce the dimensionality of the non-linear, non-convex HiC matrix data to the intrinsic dimensionality of the data, which is a 3D manifold, represented by $Z \in \mathbb{R} 3$.

In order to reconstruct the 3D structure of the genome, the architecture 300 according to FIG. 3 is proposed which fundamentally uses a neural network architecture designed as a "greater autoencoder" including a structured plurality of autoencoder units 340, 342, 344, Each of which includes an encoder unit 304, 314, 324 and a respective decoder unit 306, 316, 326, each of which is implemented as recurrent neural network (RNN).

As input to the encoder unit 304, 314, 324 a vector of the pre-processed HiC matrix 204 (compare FIG. 2) is used (as well as the status of a previous encoder unit, see below). Thus, the number of encoder units 304, 314, 324, as well as the number of decoder unit 306, 316, 326, is equal to the dimensionality of the pre-processed HiC matrix 204.

The input data 310, 320, 330 are represented as a set of features for each element in the sequence, $c = \{c_1, c_2, \ldots, c_N\}$, with $c_i \in \mathbb{R} M$, where N is the sequence length, and M is the number of features of each element. Similarly, the output sequence 312, 322, 332 is the reconstruction of the input, hence, $\hat{c}=\{\hat{c}1, \hat{c}2, \ldots, \hat{c}N\}$, with $\hat{c}i \in \mathbb{R}^M$.

Each element in the input sequence is represented by a bin in the chromosome sequence. Therefore, the input to each encoder unit 304, 314, 324 are the features of respective bins, i.e., the interactions of that bin with all other bins in the HiC matrix C. Because the matrix is symmetric, the sequence length N and the number of features M is equal; thus, the input matrix is symmetrical.

For the encoder units 304, 314, 324 Long Short-Term Memory (LSTM) neural networks are used, designed to encode the sequentiality (or sequence) in the data. The input to each encoder LSTM unit i is the feature vector of the corresponding element i, $cij=\{ci1, ci2, ci3, \ldots, ciM\}$, where cij is the contact frequency between bins i and j, with $j \in \{1, \ldots, M\}$ and the previous hidden state $h^{enc}_{i-1}=\{h^1_{i-1}, h^2_{i-1}, h^3_{i-1}\} \in \mathbb{R}^3$. The output 308, 318, 328 of the encoder cells 304, 314, 324 is the fixed low-dimensional embedding $z_i=\{x_i, y_i, z_i\} \in \mathbb{R}^3$. Hence, $$z_i = f^{enc}(c_i, h^{enc}_{i-1}) \quad (1)$$

Similarly, the decoder units 306, 316, 326 are also LSTM neural networks. The input to the decoder LSTM unit i is the 3D embedding of the corresponding element i, $z_i=\{x_i, y_i, z_i\}$ 308, 318, 328 and the hidden state of the previous decoder cell, $h^{dec}_{i-1}=\{h^1_{i-1}, h^2_{i-1}, h^M_{i-1}\} \in \mathbb{R}^M$.

The output 312, 322, 332 of the decoder cells are the fixed reconstruction of the contact frequencies $\hat{x}=\{\hat{c}^1_i, \hat{c}^2_i, \ldots, \hat{c}^{N_i}\}$. Hence, $$\hat{c}_i = g^{dec}(z_i, h^{dec}_{i-1}) = g^{dec}(f^{enc}(c_i, h^{enc}_{i-1}), h^{dec}_{i-1}) \quad (2)$$

Consequently, the sequence of embeddings and the 3D space can then be obtained from $Z=\{z_1, z_2, \ldots, z_N\}$, with $\in \mathbb{R}^3$ representing the coordinates of the bins in the predicted chromatin structure, as indicated in FIG. 3.

It may also be noted that inner state of a respective autoencoder unit—i.e., the related encoder as well as the related decoder—is fed as input to a next autoencoder unit. This is represented by the arrows 346 from an encoder to next encoder and arrow 348 from a decoder to a next decoder.

Special consideration may be given to the cost function used for the RNNs 304, 314, 324, 306, 316, 326 of the encoder units and the decoder units. The optimization process of the parameters of the RNNs—also denoted both as artificial neuron weight factors—of the structured plurality—or networks—of autoencoder units 340, 342, 344 employs a flexible combined loss function including a term for each autoencoder unit and composed of a main reconstruction loss and a few other regularizers, specific to each organism and cell type so that the genome structure is tried to be inferred. The loss function can be used across data sets of different organisms and cell types. It includes the reconstruction loss $L_{rec}$ and a distance cost $L_d$, as shown in equation 4:

$$L = L_{rec}(C, \hat{C}) + \lambda L_d(Z) \quad (4)$$

The reconstruction loss uses the known squared error loss in equation 4. This reduces the reconstruction error of the HiC contact frequency matrix:

$$Lrec(C, \hat{C}) = 1/N \Sigma_{i=1}^N (c_i - \hat{c}_i)^2 = 1/N \Sigma_{i=1}^N (c_i - g^{dec}(f^{enc}(c_i, h^{enc}_{i-1}), h^{dec}_{i-1}))^2.$$

The distance loss acts as a regularizer on the lower-bound and upper-bound of the Euclidean distance between two consecutive bins. The loss formulation is similar to a Lagrangian expression and the regularization constant can be interpreted as a Lagrangian multiplier. This is expressed in equation 5:

$$Ld(Z) = 1/(N-1) \Sigma_{i=1}^{N-1} (\max(b_{min} - \|z_i, z_{i+1}\|^2_2, 0) + \max(\|z_i, z_{i+1}\|^2_2 - b_{max}, 0)) \quad (5)$$

This way, the two forces (the deviation from the lower-bound and the deviation from the upper-bound) are pulling in opposite directions. This does not imply that the distances are it equal deviation from both lower-bounds and upper-bounds because the reconstruction costs can impose a preference towards one of the bounds. This enables to model the folding behavior of the chromosomes because the bounds can be interpreted as follows:

The lower-bound, defined by $b_{min}$, represents a fully packed folding of the chromosome bins;

the upper-bound, defined by $b_{max}$, represents a fully extended folding of the chromosome bins.

This regularizer is dependent on the resolution, because one wants to preserve the same bounds for the packing ratio across the bins in the structure at a given resolution. If one changes the resolution, one can simply scale the structure and obtain the same effect as proportionally changing the bounds.

The next section of this document is directed to a time-dependent analysis of the chromatin. As already mentioned, existing methods—even if not so elegantly as proposed here—only tried to perform a 3D analysis. Currently, research is shifting towards a four-dimensional (4D) analysis trying to acquire data and establish a pipeline for preprocessing it. By applying any of the previously discussed concepts, it is possible to obtain independent 3D structures for each of the time points.

The elegance in the proposed model lies in the fact that it is possible to incorporate in the inference process information about the structure at previous time points and, hence, perform a multi-dimensional timeseries analysis.

In order to achieve this, the weight values of the RNNs are initialized with the weight values of the ones optimized for the inference of the previous time point. This is best expressed in pseudo-code, as shown in FIG. 4. In this illustration, the arrows point to relevant lines for the time-series analysis.

Then, the model learns (is trained) the time-dependent chromatin structure starting from the structure at the previous time point. This simulates what happens to the chromatin structure when changing from one time point to the next.

One may expect that a fine granularity of time points may be required. However, this is not the case because the model of the autoencoders is still retrained using the current contact frequency information. Thus, it is not necessary that the previous time point is very close by and time, due to the fact that information from the weight factors of the previous time point is only used as initialization. In this case, when the previous time point, and thus solution, is much further, it is expected to take more time for the structured plurality of autoencoders to converge.

As results of the proposed concept to infer 3D chromatin structures using a variety of publicly available HiC and data sets, the following is presented: one example structure of the whole fission yeast genome has been analyzed. Bins of the chromosome were taken in a sequential order. As expected from prior biological knowledge, chromosomes occupy individual territories, intermingle at the boundaries of these territories and the sequence of the bin is preserved, as a 3D visualization showed. To assess the performance of the proposed concept, the predicted structures have been examined on independent data sets: a synthetic contact matrix derived from 100 hypothetical genome structures and a real HiC matrix, corresponding to measurements at different time points of the fission yeast's cell cycle.

In order to compare the results of the proposed method to the ground-truth simulated structures resorting happened before performing ensemble inference.

Starting from the synthetic HiC matrix, firstly, a population of 100 3D structures has been generated. For each pair of bins, the pairwise Euclidean distance in both populations (the 100 ground-truth structures and the ensemble of 100 predicted structures) are computed and the respective distributions are estimated. To assess the distance between these two distributions, the Wasserstein metric is employed. The same process is repeated for all pairs of bins, resulting in a distribution of Wasserstein distances, shown in FIG. 5.

As one can easily see, the distance follows a skewed distribution to the right, indicating that the distance is very low, with only a few large arrows in the tail of the distribution.

In the case of fission yeast, there are 18 pairs of distances between loci, which have been measured on experimentally by FISH imaging as known from prior art. Out of the 18 pairs of loci, 11 are intra-chromosomal and 7 are inter-chromosomal. One can use the 18 distances for validation of the predicted structures and compare with the two commonly employed algorithms, miniMDS and GEM, which is also known from prior art. To achieve this, one computes the correlation coefficients between the distances in the predicted structures and the FISH distances. The results can be seen in FIG. 6.

The following table shows the related correlations:

| method | Pearson correlation (r) |
|---|---|
| MiniMDS | 0.53 |
| GEM | 0.38 |
| REACH-3D | 0.56 |

Thus, the proposed concept (REACH-3) shows a better correlation factor than the other methods.

As summary and final advantage, it may be stated that the here proposed concept for understanding the 3D chromatin conformation is essential for decoding and interpreting the functions of a genome as a whole as well as its functional and regulatory elements, and can provide a mechanistic explanation of various biological processes in human diseases.

For completeness reasons, FIG. 7 shows a block diagram of an inference system 700 for inferring a 3D structure of a genome. The inference system 700 includes a receiving unit 702 adapted for providing an n*n matrix of genome interaction data, and an autoencoder system 704 including a structured sequence of n autoencoder units 712, 714, 716, each of which including an encoder unit and a decoder unit (not shown). A more detailed description of this portion of the inference system 700 is given in FIG. 3. Moreover, it should be noted that each of the encoder units and each of the decoder units is implemented each as a recurrent neural network unit.

The inference system 700 also includes a training module 718 adapted for training the autoencoder by feeding all n vectors of the matrix of genome interaction data to input layers of the n encoder units until the fed n vectors of genome interaction data and respective decoder outputs only differ by a predefined threshold value. The training of the auto-encoder units 712, 714, 716 is performed stepwise by using as input for an ith selected encoder unit the respective ith vector of the genome interaction data, and output values of the previous encoder unit to the selected encoder unit in the structured sequence of the n autoencoder units (compare 704 autoencoder system), and performing backpropagation within each of the plurality of autoencoder units 712, 714, 716 after all autoencoder units 712, 714, 716 have processed their respective input values.

Last but not least, the inherent system 700 includes a visualization module 720 adapted for using the output values of the encoder units for deriving a 3D model for a visualization of the genome.

Embodiments of the invention may be implemented together with virtually any type of computer, regardless of the platform being suitable for storing and/or executing program code. FIG. 8 shows, as an example, a computing system 800 suitable for executing program code related to the proposed method.

The computing system 800 is only one example of a suitable computer system, and is not intended to suggest any limitation as to the scope of use or functionality of embodiments of the invention described herein, regardless, whether the computer system 800 is capable of being implemented and/or performing any of the functionality set forth hereinabove. In the computer system 800, there are components, which are operational with numerous other general purpose or special purpose computing system environments or configurations. Examples of well-known computing systems, environments, and/or configurations that may be suitable for use with computer system/server 800 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 800 may be described in the general context of computer system-executable instructions, such as program modules, being executed by a computer system 800. Generally, program modules may include routines, programs, objects, components, logic, data structures, and so on that perform particular tasks or implement particular abstract data types. Computer system/server 800 may be practiced in distributed cloud computing environments where tasks are performed by remote processing devices that are linked through a communications network. In a distributed cloud computing environment, program modules may be located in both, local and remote computer system storage media, including memory storage devices.

As shown in the figure, computer system/server 800 is shown in the form of a general-purpose computing device. The components of computer system/server 800 may include, but are not limited to, one or more processors or processing units 802, a system memory 804, and a bus 806 that couple various system components including system memory 804 to the processor 802. Bus 806 represents one or more of any of several types of bus structures, including a memory bus or memory controller, a peripheral bus, an accelerated graphics port, and a processor or local bus using any of a variety of bus architectures. By way of example, and not limiting, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus. Computer system/ server 800 typically includes a variety of computer system readable media. Such media may be any available media that is accessible by computer system/server 800, and it includes both, volatile and non-volatile media, removable and non-removable media.

The system memory 804 may include computer system readable media in the form of volatile memory, such as random access memory (RAM) 808 and/or cache memory 810. Computer system/server 800 may further include other removable/non-removable, volatile/non-volatile computer system storage media. By way of example only, a storage system 812 may be provided for reading from and writing to a non-removable, non-volatile magnetic media (not shown and typically called a 'hard drive'). Although not shown, a magnetic disk drive for reading from and writing to a removable, non-volatile magnetic disk (e.g., a 'floppy disk'), and an optical disk drive for reading from or writing to a removable, non-volatile optical disk such as a CD-ROM, DVD-ROM or other optical media may be provided. In such instances, each can be connected to bus 806 by one or more data media interfaces. As will be further depicted and described below, memory 804 may include at least one program product having a set (e.g., at least one) of program modules that are configured to carry out the functions of embodiments of the invention.

The program/utility, having a set (at least one) of program modules 816, may be stored in memory 804 by way of example, and not limiting, as well as an operating system, one or more application programs, other program modules, and program data. Each of the operating systems, one or more application programs, other program modules, and program data or some combination thereof, may include an implementation of a networking environment. Program modules 816 generally carry out the functions and/or methodologies of embodiments of the invention, as described herein.

The computer system/server 800 may also communicate with one or more external devices 818 such as a keyboard, a pointing device, a display 820, etc.; one or more devices that enable a user to interact with computer system/server 800; and/or any devices (e.g., network card, modem, etc.) that enable computer system/server 800 to communicate with one or more other computing devices. Such communication can occur via Input/Output (I/O) interfaces 814. Still yet, computer system/server 800 may communicate with one or more networks such as a local area network (LAN), a general wide area network (WAN), and/or a public network (e.g., the Internet) via network adapter 822. As depicted, network adapter 822 may communicate with the other components of the computer system/server 800 via bus 806. It should be understood that, although not shown, other hardware and/or software components could be used in conjunction with computer system/server 800. Examples, include, but are not limited to: microcode, device drivers, redundant processing units, external disk drive arrays, RAID systems, tape drives, and data archival storage systems, etc.

Additionally, the inference system 700 for inferring a 3D structure of a genome may be attached to the bus system 806.

The descriptions of the various embodiments of the present invention have been presented for purposes of illustration, but are not intended to be exhaustive or limited to the embodiments disclosed. Many modifications and variations will be apparent to those of ordinary skills in the art without departing from the scope and spirit of the described embodiments. The terminology used herein was chosen to best explain the principles of the embodiments, the practical application or technical improvement over technologies found in the marketplace, or to enable others of ordinary skills in the art to understand the embodiments disclosed herein.

The present invention may be embodied as a system, a method, and/or a computer program product. The computer program product may include a computer readable storage medium (or media) having computer readable program instructions thereon for causing a processor to carry out aspects of the present invention.

The medium may be an electronic, magnetic, optical, electromagnetic, infrared or a semi-conductor system for a propagation medium. Examples of a computer-readable medium may include a semi-conductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-RAY), DVD and Blu-Ray-Disk.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disk read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object-oriented programming language such as Smalltalk, C++ or the like, and conventional procedural programming languages, such as the "C" programming language or similar programming languages. The computer readable program instructions may execute entirely on the user's computer, partly on the user's computer as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatuses, or another device to cause a series of operational steps to be performed on the computer, other programmable apparatus or other device to produce a computer implemented process, such that the instructions which execute on the computer, other programmable apparatuses, or another device implement the functions/acts specified in the flowchart and/or block diagram block or blocks.

The flowcharts and/or block diagrams in the figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or act or carry out combinations of special purpose hardware and computer instructions.

The terminology used herein is for the purpose of describing particular embodiments only and is not intended to limit the invention. As used herein, the singular forms "a", "an" and "the" are intended to include the plural forms as well, unless the context clearly indicates otherwise. It will further be understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or steps plus function elements in the claims below are intended to include any structure, material, or act for performing the function in combination with other claimed elements, as specifically claimed. The description of the present invention has been presented for purposes of illustration and description, but is not intended to be exhaustive or limited to the invention in the form disclosed. Many modifications and variations will be apparent to those of ordinary skills in the art without departing from the scope and spirit of the invention. The embodiments are chosen and described in order to best explain the principles of the invention and the practical application, and to enable others of ordinary skills in the art to understand the invention for various embodiments with various modifications, as are suited to the particular use contemplated.

What is claimed is:

1. A computer-implemented method for inferring a 3D structure of a genome, the computer-implemented method comprising:

providing a n*n matrix of genome interaction data;

operating an autoencoder comprising a structured sequence of n autoencoder units, each of which comprising an encoder unit and a decoder unit, wherein each vector of the n*n matrix of genome interaction data represents contact information of a bin of the genome, such that each bin of the genome is processed independently of contact data for another bin in the genome by feeding each bin to a separate one of the encoder units, wherein each of the encoder units and each of the decoder units is implemented each as a recurrent neural network unit;

training the autoencoder by feeding all n vectors of the matrix of genome interaction data to input layers of the n encoder units until the fed n vectors of genome interaction data and respective decoder outputs only differ by a predefined threshold value, wherein the training of the auto-encoder units is performed stepwise by:

using as input for an ith selected encoder unit the respective ith vector of the genome interaction data, and output values of the previous encoder unit to the selected encoder unit in the structured sequence of n autoencoder units, using as input for an ith selected decoder unit output values of the ith encoder unit, and output values of the previous decoder unit to the selected decoder unit in the structured sequence of n autoencoder units, and performing backpropagation within each of the plurality of autoencoder units after all autoencoder units have processed their respective input values, and using the output values of the encoder units for deriving a 3D model for a visualization of the genome.

2. The computer-implemented method according to claim 1, wherein the genome interaction data originate from a publicly available source.

3. The computer-implemented method according to claim 1, wherein the matrix of the genome interaction data originate from an HiC experiment.

4. The computer-implemented method according to claim 1, wherein the output values of the encoder units are used as coordinates in 3-dimensional space.

5. The computer-implemented method according to claim 1, wherein each of the recurrent neural networks units is an LSTM neural network unit.

6. The computer-implemented method according to claim 1, wherein a loss function of each of the encoder units and decoder units is cell-type specific.

7. The computer-implemented method according to claim 1, wherein a loss function comprises a reconstruction cost factor and a distance cost factor.

8. The computer-implemented method according to claim 7, wherein the reconstruction cost factor is determined according to a mean-square error loss calculation.

9. The computer-implemented method according to claim 1, wherein a distance cost factor acts as a regularizer on the lower-bound and upper-bound of the Euclidean distance between two consecutive bins of a genome.

10. The computer-implemented method according to claim 1, also comprising
providing a time series of genome interaction data to the autoencoder, and
using resulting time-dependent output values of the encoder units for deriving a time-dependent 3D model for a visualization of the genome.

11. The computer-implemented method according to claim 10, wherein the providing the time series of genome interaction data to the autoencoder also comprises,
initializing, during training, weight factors of the encoder units and decoder units with respective weight factors of a previous time point of the time series of genome interaction data.

12. An inference system for inferring a 3D structure of a genome, the inference system comprising:
a receiving unit adapted for providing a n*n matrix of genome interaction data;
an autoencoder system comprising a structured sequence of n autoencoder units, each of which comprising an encoder unit and a decoder unit, wherein each vector of the n*n matrix of genome interaction data represents contact information of a bin of the genome, such that each bin of the genome is processed independently of contact data for another bin in the genome by feeding each bin to a separate one of the encoder units, wherein each of the encoder units and each of the decoder units is implemented each as a recurrent neural network unit;
a training module adapted for training the autoencoder by feeding all n vectors of the matrix of genome interaction data to input layers of the n encoder units until the fed n vectors of genome interaction data and respective decoder outputs only differ by a predefined threshold value;
wherein the training of the auto-encoder units is performed stepwise by:
using as input for an ith selected encoder unit the respective ith vector of the genome interaction data, and output values of the previous encoder unit to the selected encoder unit in the structured sequence of n autoencoder units,
using as input for an ith selected decoder unit output values of the ith encoder unit, and output values of the previous decoder unit to the selected decoder unit in the structured sequence of n autoencoder units, and
performing backpropagation within each of the plurality of autoencoder units after all autoencoder units have processed their respective input values; and
a visualization module adapted for using the output values of the encoder units for deriving a 3D model for a visualization of the genome.

13. The inference system according to claim 12, wherein the genome interaction data originate from a publicly available source.

14. The inference system according to claim 12, wherein the matrix of the genome interaction data originate from an HiC experiment.

15. The inference system according to claim 12, wherein the output values of the encoder units are usable as coordinates in 3-dimensional space.

16. The inference system according to claim 12, wherein each of the recurrent neural networks units is an LSTM neural network unit.

17. The inference system according to claim 12, wherein a loss function of each of the encoder units and decoder units is cell-type specific.

18. The inference system according to claim 12, wherein a loss function comprises a reconstruction cost factor and a distance cost factor.

19. The inference system according to claim 18, wherein the reconstruction cost factor is determined according to a mean-square error loss calculation.

20. The inference system according to claim 12, wherein a distance cost factor acts as a regularizer on the lower-bound and upper-bound of the Euclidean distance between two consecutive bins of a genome.

21. The inference system according to claim 12, wherein the receiving unit is also adapted for providing a time series of genome interaction data to the autoencoder, and
wherein the visualization module adapted is also adapted for using resulting time-dependent output values of the encoder units for deriving a time-dependent 3D model for a visualization of the genome.

22. The inference system according to claim 21, wherein the providing the time series of genome interaction data to the autoencoder also comprises:
initializing, during training, weight factors of the encoder units and decoder units with respective weight factors of a previous time point of the time series of genome interaction data.

23. A computer program product for inferring a 3D structure of a genome, the computer program product comprising a computer readable storage medium having program instructions embodied therewith, said program instructions being executable by one or more computing systems or controllers to cause said one or more computing systems to:
provide a n*n matrix of genome interaction data;
operate an autoencoder comprising a structured sequence of n autoencoder units, each of which comprising an encoder unit and a decoder unit, wherein each vector of the n*n matrix of genome interaction data represents contact information of a bin of the genome, such that each bin of the genome is processed independently of contact data for another bin in the genome by feeding each bin to a separate one of the encoder units, wherein each of the encoder units and each of the decoder units is implemented each as a recurrent neural network unit;

train the autoencoder by feeding all n vectors of the matrix of genome interaction data to input layers of the n encoder units until the fed n vectors of genome interaction data and respective decoder outputs only differ by a predefined threshold value;

wherein the training of the auto-encoder units is performed stepwise by:
  using as input for an ith selected encoder unit the respective ith vector of the genome interaction data, and output values of the previous encoder unit to the selected encoder unit in the structured sequence of n autoencoder units,
  using as input for an ith selected decoder unit output values of the ith encoder unit, and output values of the previous decoder unit to the selected decoder unit in the structured sequence of n autoencoder units, and perform backpropagation within each of the plurality of autoencoder units after all autoencoder units have processed their respective input values, and use the output values of the encoder units for deriving a 3D model for a visualization of the genome.

\* \* \* \* \*